(12) United States Patent
Vortman et al.

(10) Patent No.: US 7,611,462 B2
(45) Date of Patent: Nov. 3, 2009

(54) ACOUSTIC BEAM FORMING IN PHASED ARRAYS INCLUDING LARGE NUMBERS OF TRANSDUCER ELEMENTS

(75) Inventors: Kobi Vortman, Haifa (IL); Shuki Vitek, Haifa (IL); Avner Ezion, Haifa (IL)

(73) Assignee: Insightec-Image Guided Treatment Ltd., Tirat Carmel (IL)

( * ) Notice: Subject to any disclaimer, the term of this patent is extended or adjusted under 35 U.S.C. 154(b) by 751 days.

(21) Appl. No.: 10/443,549

(22) Filed: May 22, 2003

(65) Prior Publication Data

US 2004/0236253 A1 Nov. 25, 2004

(51) Int. Cl.
*A61B 8/00* (2006.01)
(52) U.S. Cl. ............... 600/437; 600/439; 600/447; 600/459; 367/138; 342/374
(58) Field of Classification Search ............... 600/407, 600/408, 437–461; 601/2–4; 367/7, 11, 367/138; 342/374
See application file for complete search history.

(56) References Cited

U.S. PATENT DOCUMENTS

| | | | |
|---|---|---|---|
| 4,505,158 A | | 3/1985 | Questo |
| 5,329,930 A | * | 7/1994 | Thomas et al. ............ 600/447 |
| 5,379,642 A | * | 1/1995 | Reckwerdt et al. ......... 73/625 |
| 6,042,556 A | * | 3/2000 | Beach et al. ............... 601/3 |
| 6,128,958 A | * | 10/2000 | Cain ......................... 73/626 |
| 6,506,154 B1 | * | 1/2003 | Ezion et al. ............... 600/437 |
| 6,719,694 B2 | * | 4/2004 | Weng et al. ............... 600/439 |
| 6,951,540 B2 | * | 10/2005 | Ebbini et al. ............. 600/437 |
| 7,175,599 B2 | * | 2/2007 | Hynynen et al. ........... 600/443 |
| 2004/0210134 A1 | * | 10/2004 | Hynynen et al. ........... 600/439 |
| 2005/0096542 A1 | * | 5/2005 | Weng et al. ............... 600/439 |

FOREIGN PATENT DOCUMENTS

| | | |
|---|---|---|
| EP | 0 031 614 | 7/1981 |
| EP | 0 272 347 | 8/1988 |
| EP | 0 875 203 | 11/1998 |
| WO | WO 01/80709 | 11/2001 |

OTHER PUBLICATIONS

PCT International Search Report for PCT/IB2004/001512, Applicant: Insightec—Image Guided Treatment Ltd, Forms PCT/ISA/210 and 220, dated Sep. 7, 2004 (8 pages).
PCT Written Opinion of the International Search Authority for PCT/IB2004/001512, Applicant: Insightec—Image Guided Treatment Ltd, Form PCT/ISA/237, dated Sep. 7, 2004 (5 pages).

* cited by examiner

*Primary Examiner*—Long V Le
*Assistant Examiner*—Sanjay Cattungal
(74) *Attorney, Agent, or Firm*—Goodwin Procter LLP

(57) ABSTRACT

A focused ultrasound system includes a transducer array, a controller for providing drive signals to the transducer array, and a switch. The transducer array includes a plurality of "n" transducer elements, and the controller includes a plurality of "m" output channels providing sets of drive signals having respective phase shift values, "m" being less than "n." The switch is coupled to the output channels of the controller and to the transducer elements, and is configured for connecting the output channels to respective transducer elements. The controller may assign the transducer elements to respective output channels based upon a size and/or shape of a desired focal zone within the target region, to steer or otherwise move a location of the focal zone, and/or to compensate for tissue aberrations caused by tissue between the transducer array and the focal zone, geometric tolerances and/or impedance variations of the transducer elements.

24 Claims, 3 Drawing Sheets

| TRANSDUCER ELEMENT | DESIRED PHASE SHIFT |
|---|---|
| 1 | 5° |
| 2 | 30° |
| 3 | 84° |
| 4 | 10° |
| 5 | 40° |
| 6 | 100° |
| ⋮ | ⋮ |
| n | 350° |

FIG. 3A

| OUTPUT CHANNEL | PHASE SHIFT | TRANSDUCER ELEMENTS | | | | | | |
|---|---|---|---|---|---|---|---|---|
| | | 1 | 2 | 3 | 4 | 5 | 6 | ... n |
| 1 | 36° | | 30° | | | 40° | | |
| 2 | 72° | | | 84° | | | | |
| 3 | 108° | | | | | | 100° | |
| ⋮ | ⋮ | | | | | | | |
| 10 | 360° | 5° | | | 10° | | | 350° |

FIG. 3B

| SWITCH INPUT | SWITCH OUTPUT | | | | | | |
|---|---|---|---|---|---|---|---|
| | 1 | 2 | 3 | 4 | 5 | 6 | ... n |
| 1 | | X | | | X | | |
| 2 | | | X | | | | |
| 3 | | | | | | X | |
| ⋮ | | | | | | | |
| 10 | X | | | X | | | X |

FIG. 3C

ACOUSTIC BEAM FORMING IN PHASED ARRAYS INCLUDING LARGE NUMBERS OF TRANSDUCER ELEMENTS

FIELD OF THE INVENTION

The present invention relates generally to systems and methods for delivering acoustic energy into a body, and more particularly to systems and methods for focusing acoustic energy transmitted from a transducer array including a large number of transducer elements.

BACKGROUND

Focused ultrasound systems have been suggested for delivering acoustic energy into a tissue region within a patient, such as a cancerous or benign tumor, to coagulate or otherwise treat the tissue region with thermal energy. For example, a piezoelectric transducer located outside the patient's body may be used to focus high intensity acoustic waves, such as ultrasonic waves (acoustic waves with a frequency greater than about twenty kilohertz (20 kHz)), at an internal tissue region of a patient to treat the tissue region. The acoustic waves may be used to ablate a tumor, thereby eliminating the need for invasive surgery. Such an acoustic transducer system is disclosed in U.S. Pat. No. 4,865,042 issued to Umemura et al.

When delivering acoustic energy, it is useful to control the shape of a "focal zone" (the volume of tissue treated when the acoustic energy is focused into a tissue region), to control "focal depth" (the distance from the transducer to the focal zone), and/or to correct for tissue aberrations that may be caused by intervening tissue between the transducer and the tissue region. It is also desirable to steer the acoustic energy away from a central axis of the transducer, e.g., at large steering angles relative to the central axis.

To facilitate steering acoustic energy, it is desirable to make the transducer elements as small as possible, preferably on the order of the wavelength of the acoustic energy transmitted by the transducer elements. For example, for acoustic energy having a frequency of one Megahertz (1 MHz), it would be desirable to provide transducer elements having a width or other maximum cross-section of less than one millimeter (1.0 mm). For a relatively large area transducer array, the total number of such transducer elements required would become very large, i.e., requiring hundreds or even thousands of transducer elements.

The problem with providing so many transducer elements is that individual sets of drive signals must be delivered to each transducer element in order for the transducer elements to transmit acoustic energy. Thus, hundreds or thousands of wires or cables would be required to deliver the drive signals to the transducer elements. The resulting system would be complicated and expensive to implement.

Accordingly, systems and methods for delivering acoustic energy from transducer arrays including many transducer elements would be useful.

SUMMARY OF THE INVENTION

The present invention is directed to systems and methods for delivering acoustic energy from a transducer array, and more particularly to systems and methods for focusing and/or steering acoustic energy from a transducer array including a large number of transducer elements, preferably into a body of a patient for ablating or otherwise treating tissue with the patient's body.

In accordance with one aspect of the present invention, a system is provided for focusing acoustic energy towards a target region that includes a transducer array, a controller for providing drive signals to the transducer array, and a switch. The transducer array may include a plurality of "n" transducer elements, and the controller may include a plurality of "m" output channels providing sets of drive signals having respective phase shift values, "m" being less than "n."

The switch, e.g., a cross-point matrix or a multistage interconnection network ("MIN"), may be coupled to the output channels of the controller and to the transducer elements. The switch may be configured for connecting output channels to respective transducer elements in order to provide respective sets of drive signals to the respective transducer elements, whereby acoustic energy transmitted by the transducer array may be focused in a desired manner. In one embodiment, the controller may be coupled to the switch for configuring the switch in order to connect the output channels to the respective transducer elements.

Using a switch with "m" drive channels to control drive signals provided to a relatively large number of "n" transducer elements may substantially minimize the complexity of the system, since relatively few drive channels may be needed for a relatively large number of transducer elements. It may also allow complex phase patterns to be created in a sub-set of transducer elements or using the entire transducer array, while using a limited number of input drive channels. In addition, because a limited number of drive channels deliver power to a relatively large number of transducer elements, the drive channels may be loaded substantially evenly, as desired for statistically even phase distribution.

The controller may be configured for assigning each of the transducer elements to a respective output channel based upon one or more parameters related to a course of treatment of a target tissue region using the transducer array. For example, the controller may assign the transducer elements to respective output channels based upon a size of a focal zone within the target region, a shape of the focal zone, axial and/or angular location of the focal zone, impedances of the transducer elements, and/or tissue aberrations caused by tissue between the transducer array and the focal zone.

In accordance with another aspect of the present invention, a transducer array is provided for delivering acoustic energy to a target region that includes a plurality of "n" transducer elements arranged on one or more substrates, and a switch coupled to the transducer elements. The switch may be coupled to the substrate(s), e.g., via electrical connections that are flexible enough not to impact substantially the acoustic characteristics of the transducer array.

The switch may include a plurality of "m" input channels and "n" output channels coupled to the transducer elements, "m" being less than "n." Each input channel of the switch may be connectable to a controller for transferring only selected drive signals including respective phase shift values, the switch configured to couple the input channels to respective transducer elements in order to provide drive signals to the respective transducer elements, whereby acoustic energy transmitted by the transducer elements may be focused in a desired manner.

In one embodiment, the transducer array may include a single substrate, and the switch may be mounted to the substrate. Alternatively, the transducer array may include a plurality of substrates that may be fixed or adjustable physically relative to one another. Each substrate may include "$n_i$" transducer elements, which may be selectively connected to a subset of the "m" input channels, "$m_k$," or to all of the "m" input channels, where the total number of all transducer elements is "n" ($\Sigma n_i = n$).

In accordance with yet another aspect of the present invention, a method is provided for delivering acoustic energy from a transducer array comprising a plurality of "n" transducer elements. One of "m" phase shift values may be assigned to each of the transducer elements, "m" being less than "n." For example, the phase shift values may be assigned to the transducer elements to steer the focal zone within the target region relative to a central axis of the transducer array. In addition, or alternatively, the phase shift values may be assigned to the transducer elements in order to focus and/or steer the acoustic energy at multiple focal zones within the target tissue region.

The "m" sets of drive signals may be delivered to the transducer array, each set of drive signals including a respective phase shift value selected from the "m" phase shift values. The sets of drive signals may be connected to respective transducer elements based upon the phase shift values assigned to the respective transducer elements, whereby acoustic energy transmitted by the transducer elements may be focused in a desired manner towards a target region. For example, the transducer array may be disposed adjacent to a patient's body, and the acoustic energy may be transmitted into the body towards a focal zone within the target region, e.g., for sufficient time to ablate tissue within the target region. Optionally, the configuration of the switch may be reconfigured dynamically during a procedure, e.g., to move the focal zone and/or compensate for parameters encountered during the procedure.

In accordance with still another aspect of the present invention, a method is provided for delivering acoustic energy from a transducer array including a plurality of "n" transducer elements to a target region. "M" sets of drive signals may be provided, each set of drive signals including a respective phase shift value selected from "m" phase shift values, "m" being less than "n." A first set of the drive signals may be connected to a first plurality of the transducer elements, and a second set of the drive signals may be connected to a second plurality of the transducer elements, whereby acoustic energy is transmitted by the first and second plurality of transducer elements and focused in a desired manner into the target region.

Preferably, each of the "m" sets of drive signals is connected to a plurality of the "n" transducer elements, whereby each of the transducer elements is connected to one of the sets of drive signals. Each of the transducer elements may be connected to one of the sets of drive signals at least partially based upon phase shift values assigned to the transducer elements based upon at least one of a size, shape, and/or location of a focal zone within the target region, to compensate for tissue aberrations that may occur along an acoustic path from each of the transducer elements to the focal zone, to set equal power distribution between drive channels, and/or to compensate for impedance variations between the transducer elements.

Other objects and features of the present invention will become apparent from consideration of the following description taken in conjunction with the accompanying drawings.

BRIEF DESCRIPTION OF THE DRAWINGS

Preferred embodiments of the present invention are illustrated by way of example, and not by way of limitation, in the figures of the accompanying drawings, in which like reference numerals refer to like components, and in which:

FIGS. 3A-3C are exemplary tables, showing desired phase shift values for transducer elements of a transducer array, associating the desired phase shift values with phase shift values assigned to output channels of a driver, and a switch configuration for connecting the transducer elements to respective output channels, respectively.

DETAILED DESCRIPTION OF PREFERRED EMBODIMENTS

Figure 1:
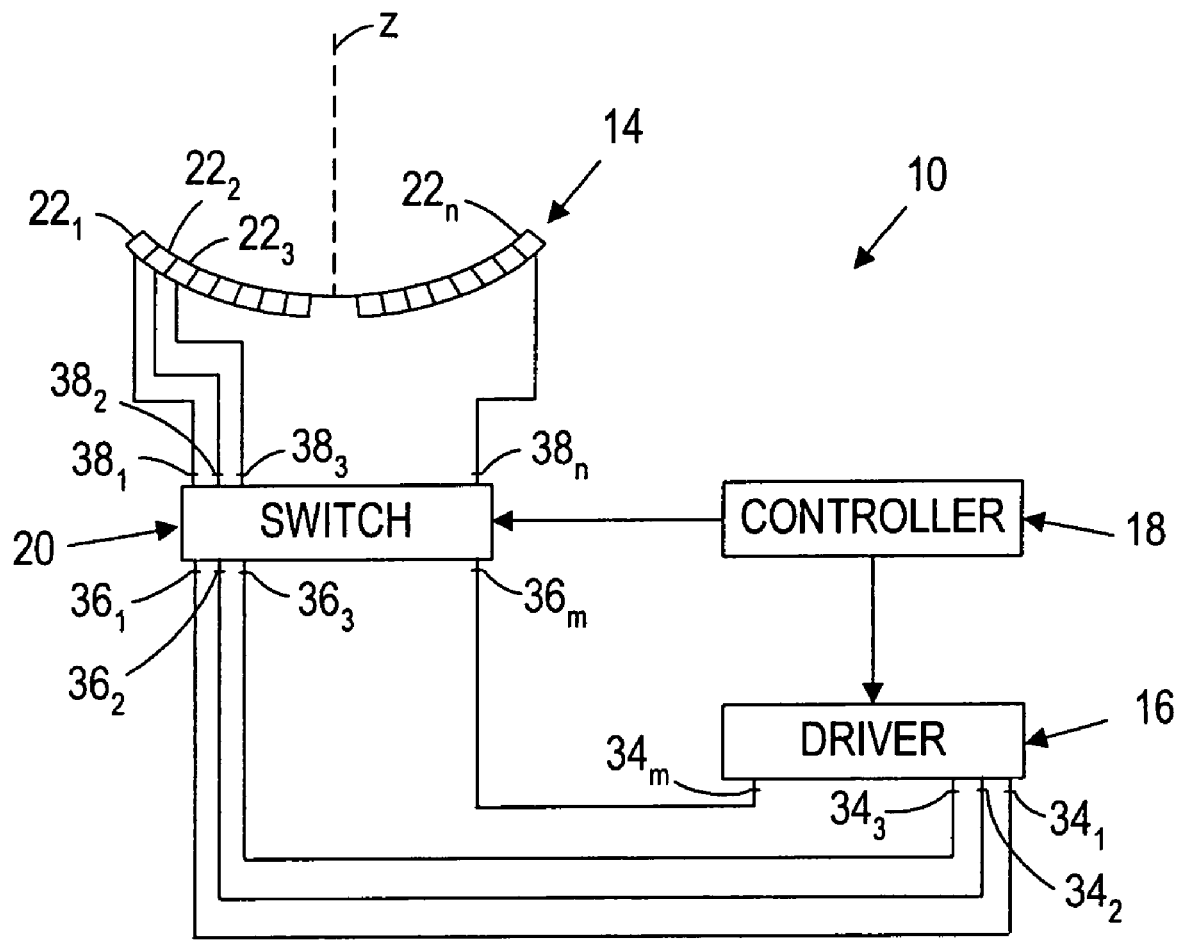
FIG. 1 is a schematic diagram of a focused ultrasound system, in accordance with the present invention.
Figure 2:
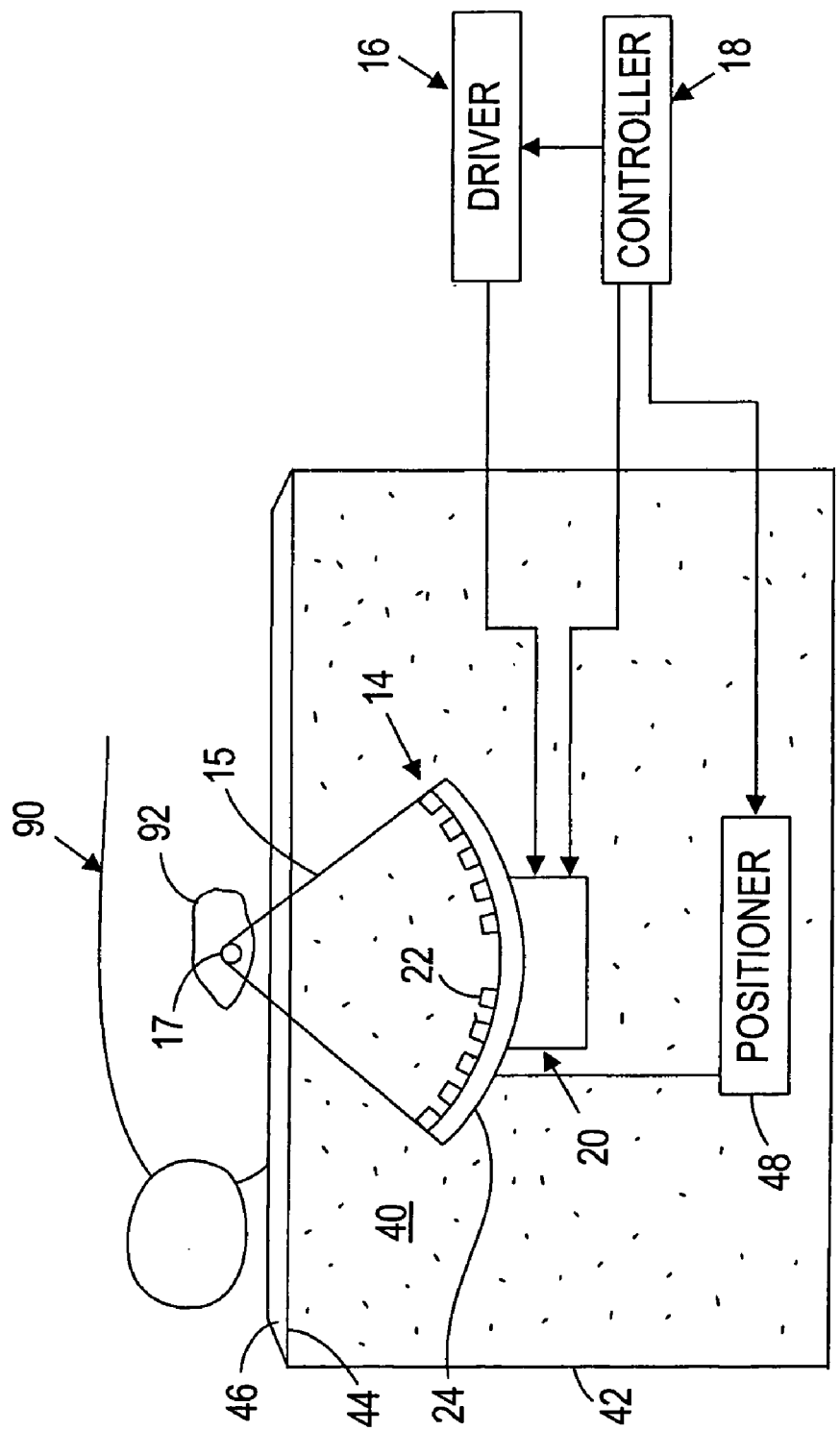
FIG. 2 is a schematic side view of a patient on a water-filled table being treated using a focused ultrasound system, such as that shown in FIG. 1.

Turning now to the drawings, FIGS. 1 and 2 depict an exemplary embodiment of a focused ultrasound system 10, including a transducer array 14, a driver 16, a controller 18, and a switch 20, in accordance with the present invention. As best seen in FIG. 2, the transducer array 14 may deliver acoustic energy represented by acoustic beam 15 into a target region 92, e.g., a benign or malignant tumor or other tissue volume, within a patient's body 90, to ablate or otherwise treat tissue within the target region 92. As explained further below, the switch 20 connects the transducer array 14 to the driver 16 and/or to the controller 18 in order to steer and/or focus the acoustic energy transmitted by the transducer array 14 in a desired manner.

With particular reference to FIG. 1, the transducer array 14 generally includes multiple transducer elements 22 arranged in a pattern on a substrate 24. The substrate 24 may be a frame, a planar or curved structure, and the like, onto which the transducer elements 22 may be mounted or otherwise provided. In one embodiment, the transducer array 14 may have a concave or bowl shape, such as a "spherical cap" shape, i.e., having a substantially constant radius of curvature such that the transducer array 14 has an inside surface defining a portion of a sphere, although alternatively, the substrate 24 may define a non-spherical surface. For example, the transducer array 14 may have an outer diameter between about eight and sixteen centimeters (8-16 cm), and a radius of curvature between about eight and twenty centimeters (8-20 cm). Alternatively, the transducer array 14 may have a substantially flat configuration (not shown), may include an outer perimeter that is generally circular, and/or may have a square, linear, hexagonal or other symmetrical or asymmetrical shape (not shown).

The transducer array 14 may be divided into any desired number "n" of transducer elements $22_1$, $22_2$, $22_3$, ... $22_n$, as seen in FIG. 1, and/or into a plurality of subsets of transducer elements, each with a plurality of transducer elements. For example, the transducer array 14 may be divided into concentric rings and/or circumferential sectors to provide the transducer elements 22. In one embodiment, the transducer array 14 may include between ten and forty (10-40) rings and between four and sixteen (4-16) sectors. In alternative embodiments, the transducer 14 may include transducer elements 22 having a variety of geometric shapes, such as hexagons, triangles, circles, squares, and the like (not shown).

The transducer elements 22 may be disposed about a central axis "z," preferably but not necessarily, in a substantially uniform or symmetrical configuration. Preferably, although not necessarily, the transducer elements 22 have substantially the same surface area as one another and/or may have similar or different sizes and shapes than one another. Additional information on the construction of transducer arrays appropriate for use with the present invention may be found, for example, in co-pending application Ser. No. 09/884,206, filed Jun. 19, 2000. The disclosures of this application and any references cited therein are expressly incorporated herein by reference.

A transducer array 14 in accordance with the present invention may include many transducer elements, e.g., hundreds or thousands of transducer elements built as a single dish, or as an assembly of many individual tiles, assembled into a structure to provide a combined array. Preferably, the transducer array 14 includes between about two hundred and ten thousand (200-10,000) transducer elements 22. The transducer elements 22 may have a width, diameter, or other maximum cross-sectional dimension across their surface area that is on the order of the wavelength of the acoustic energy that is transmitted by the transducer elements 22. For example, the transducer elements 22 may have a cross-sectional dimension between about 0.8 and seven millimeters (0.8-7 mm), which are on the order of the wavelength of ultrasonic energy between about two and 0.2 Megahertz (2-0.2 MHz), respectively. The specific number of transducer elements and their sizes, however, is not important to the present invention, and the systems and methods discussed herein may be applicable to a transducer array 14 including a variety of different configurations of transducer elements 22.

The driver 16 and/or the controller 18 may be coupled to the transducer array 14 via the switch 20 for causing the transducer elements 22 to transmit acoustic energy. Generally, the driver 16 includes an oscillator and/or other component(s) (not shown) enabling the driver 16 to generate electrical drive signals, which may be controlled by the controller 18. The driver 16 may generate drive signals in the ultrasound frequency spectrum that may be as low as twenty kilohertz (20 kHz), and that typically range from about 0.3 to three Megahertz (0.3-3.0 MHz). Preferably, the driver 16 provides radio frequency (RF) drive signals, for example, between about 0.3-3.0 MHz, and more preferably between about 0.5-2.5 MHz. When the drive signals are delivered to the transducer array 14, the transducer elements 22 convert the electrical drive signals into vibrational energy, as represented by the acoustic beam 15. Exemplary drivers and/or controllers that may be used to generate sets of drive signals are disclosed in U.S. Pat. No. 6,506,154, the disclosure of which is expressly incorporated herein by reference.

The driver 16 and/or controller 18 may be separate from or integral components of the transducer array 14, and/or may be separate components from or integral with one another. It will be appreciated by one skilled in the art that the operations performed by the driver 16 and/or controller 18 may be performed by one or more controllers, processors, and/or other electronic components, including software or hardware components.

As shown in FIG. 1, the driver 16 includes a number "m" of output channels 34 that provide respective sets of drive signals ($s_1, s_2, s_3, \ldots s_m$) having respective phase shift values ($\theta_1, \theta_2, \theta_3, \ldots \theta_m$). The number "m" of output channels 34 is generally substantially less than the number "n" of transducer elements 22, and preferably "m" is orders of magnitude smaller than "n." For example, "n"/"m" could be between about ten and one hundred (10-100), or even more than one hundred (100).

The switch 20 generally includes an "m" number of inputs 36, an "n" number of outputs 38, and a plurality of switches (not shown) therein. The "m" output channels 34 from the driver 16 may be coupled to the "m" inputs 36 of the switch 20, respectively, and the "n" outputs 38 of the switch 20 may be coupled to the "n" transducer elements 22, respectively. Thus, the switch 20 may allow respective inputs 36 to be selectively connected to one or more respective outputs 38, thereby delivering sets of drive signals with different phase shift values to respective transducer elements 22.

The switch 20 may be a cross-point matrix, a multistage interconnection network ("MIN"), or other switching device enabling multiple inputs to be selectively connected to one or more respective outputs, as is known in the art. Preferably, the switch 20 is mounted to the transducer array 14, e.g., to the substrate 24 opposite the transducer elements 22, as shown in FIG. 2. Wires, cables, conductive paths, or other conductors (generally referred to herein as "leads," not shown) may extend between the outputs 38 of the switch 20 and respective transducer elements 22, e.g., along the substrate 24 or otherwise contained within the transducer array 14. The leads should electrical connectivity, while mechanically isolating the transducer vibrating elements from the substrate 24. Alternatively, the switch 20 may be mounted in close proximity to the transducer array 14, i.e., not directly mounted to the substrate 24.

Wires or other leads, e.g., within one or more cables (also not shown), may extend from the inputs 36 of the switch 20 to the driver 16. This arrangement may substantially simplify wiring of the transducer array 14, since only "m" leads are required for the cable(s) connecting the transducer array 14 to the driver 16, rather than "n" leads, as would be required if each transducer element 22 were separately connected to the driver 16.

If the system 10 is used in conjunction with magnetic resonance imaging ("MRI"), parts of the switch 20, including any leads should be made from nonmagnetic materials, as is well known to those skilled in the art optionally, the leads may include one or more connectors (not shown) for detachably connecting them to any of the components described herein, as is known in the art.

The controller 18 may control the driver 16, e.g., to control one or more characteristics of the drive signals generated by the driver 16. For example, the controller 18 may control an amplitude of the drive signals, and, consequently, the intensity or power of the acoustic waves transmitted by the transducer 14, as is known in the art, and/or the phase allocation to each of the "m" leads 34 leaving the driver 16.

In addition, the controller 18 may also control and/or assign phase shift values to the drive signals in order to steer and/or focus the acoustic energy in a desired manner. For example, the controller 18 may divide a full cycle (360° or $2\pi$ radians) by the number of output channels 34 of the driver 16 and assign sequential phase shift values, e.g., between 0° and 360° to the sets of drive signals. Thus, for a driver including ten (10) output channels, the phase shift values assigned to the sets of drive signals and output channels could be as follows: $s_1: \theta_1=36°, s_2: \theta_2=72°0, s_3: \theta_3=108°, \ldots s_{10}: \theta_{10}=360°$. It will be appreciated that the controller 18 may assign phase shift values using other methodologies, and cause the driver 16 to generate sets of drive signals based upon the assigned phase shift values.

Further, the controller 18 may be configured to generate one or more tables relating sets of drive signals to the transducer elements 22 that may be used by the system 10. The controller 18 may include one or more processors (not shown) for generating the data for the tables, and/or memory (also not shown) for storing the one or more tables.

For example, the controller 18 may generate respective desired phase shift values for the transducer elements 22 based upon parameters for a particular treatment, and create a first table of desired phase shift values for the transducer elements 22. The data in the first table may be based upon a desired focal depth, a desired focal zone shape, compensation for tissue aberrations encountered during a particular treatment, compensation for variances in the relative impedance of the transducer elements, and/or compensation for geometric inaccuracies in positioning the transducer elements 22 relative to one another on the transducer array 14. A hypothetical set of desired phase shift values for a transducer array including "n" elements is shown in FIG. 3A.

Alternatively, it will be appreciated that separate tables may be generated for one or more of these parameters, e.g., for different beam paths, focal zone locations, and/or focal depths. During a procedure, one or more sets of tables may be loaded, e.g., to reconfigure the switch 20 during a procedure. This may provide the controller 18 with even greater flexibility to switch steering and focusing dynamically.

First, the controller 18 may assign phase shift values to each of the transducer elements 22 based upon a desired location for the focal zone 17 of the transducer array 14. For example, the controller 18 may assign phase shift values to transducer elements 22 based upon their circumferential location around the central axis "z" and/or their radial distance from the central axis "z." These phase shift values may change the size and/or shape of the resulting focal zone 17, and/or may adjust the focal depth, as is known in the art. In addition, the controller 18 may assign phase shift values to the transducer elements 22 that move the focal zone laterally relative to the central axis "z," i.e., to steer the focal zone away from the central axis "z," and/or to generate multiple focal zones simultaneously. Exemplary systems and methods for achieving such steering are disclosed in co-pending application Ser. No. 09/724,611, filed Nov. 28, 2000. The disclosures of this reference and any others cited therein are expressly incorporated herein by reference.

Second, the controller 18 may compensate for tissue aberrations, i.e., phase shifts that may occur due to the acoustic energy from respective transducer elements 22 traveling along different acoustic paths having different densities, e.g., when the acoustic energy passes through different tissue structures. The controller 18 may analyze an acoustic path from each of the transducer elements 22 through intervening tissue structures to the target region 92, e.g., using magnetic resonance imaging, ultrasound imaging, and the like. Exemplary systems and methods for compensating for tissue aberrations are disclosed in application Ser. Nos. 09/724,817, filed Nov. 28, 2000, and Ser. No. 10/190,787, filed Jul. 8, 2002, the disclosures of which are expressly incorporated herein by reference. The phase shift values for compensating for tissue aberrations may be added to any other phase shift values assigned by the controller 18, e.g., those desired to control the size and/or location of the resulting focal zone, to provide phase corrections correcting for physical tolerances in the transducer structure, and/or to compensate for impedance variations between the different elements, as is known in the art.

Once the desired phase shift values for the transducer elements 22 are known, the controller 18 may assign sets of drive signals to the transducer elements 22 to create a second table of assigned drive signal-transducer element relationships. For example, the controller 18 may compare the phase shift values of the sets of drive signals to the desired phase shift values for the transducer elements 22, and assign each of the transducer elements 22 to a set of drive signals that has a phase shift value that approximates the desired phase shift value for the respective transducer element. The controller 18 may round the desired phase shift value for each of the transducer elements 22 off to the nearest phase shift value corresponding to one of the sets of drive signals.

For example, using the exemplary ten phase shift values and associated sets of drive signals discussed above, if the desired phase shift value of a given transducer element was 30°, the transducer element would be assigned to $s_1$: $\theta_1=36°$, while a transducer with a desired phase shift value of 84° would be assigned to $s_2$: $\theta_2=72°$. Alternatively, the desired phase shift values could be truncated or associated with respective sets of drive signals using other methodologies. An exemplary table showing transducer elements assigned to respective output channels, and consequently, respective phase shift values is shown in FIG. 3B.

Once each of the transducer elements 22 has been assigned to a respective set of drive signals, the controller 18 may generate a third table to control the switch 20, e.g., based upon the drive signal-transducer element assignments in the second table. For example, if the switch 20 is a cross-point matrix, the third table may instruct the cross-point matrix to configure its switches in a particular manner to connect the inputs 36 to respective outputs 38 in order to connect the transducer elements 22 to the output channels 34 corresponding to their assigned sets of drive signals. The controller 18 may control the switch 20 directly, or the switch 20 may include its own controller (not shown). An exemplary table identifying inputs and outputs of a switch to connect to one another is shown in FIG. 3B, based upon the data from FIGS. 3A and 3B discussed above. optionally, the controller 18 may also control a physical position or orientation of the transducer array 14. For example, as shown in FIG. 2, the system 10 may include a mechanical positioner 48 connected to the transducer array 14 that may move the transducer array 14 in one or more dimensions, and preferably in any of three orthogonal directions. Exemplary transducers and positioning systems are disclosed in co-pending applications Ser. Nos. 09/556,095 and 09/557,078, both filed Apr. 21, 2000, and Ser. No. 09/628,964, filed Jul. 31, 2000. The disclosures of these references and any others cited therein are expressly incorporated herein by reference. Thus, the transducer array 14 may be focused electronically, mechanically, or using a combination of the two, and/or the focus zone may be moved within the target 92 electronically, mechanically, or using a combination of the two.

As shown in FIG. 2, the transducer array 14 may be mounted within a casing or chamber 40 filled with degassed water or similar acoustically propagating fluid. The chamber 40 may be located within a table 42 upon which a patient 90 may be disposed, or within a fluid-filled bag mounted on a movable arm that may be placed against a patient's body (not shown). The top of the table 42 generally includes a flexible membrane 44 that is substantially transparent to ultrasound, such as mylar, polyvinyl chloride (PVC), or other suitable plastic material. A fluid-filled bag 46 may be provided on the membrane 44 that may conform easily to the contours of the patient 90 disposed on the table 42, thereby acoustically coupling the patient 90 to the transducer array 14 within the chamber 40. In addition or alternatively, acoustic gel, water, or other fluid (not shown) may be provided between the patient 90 and the membrane 44 to facilitate further acoustic coupling between the transducer array 14 and the patient 90, as is known to those skilled in the art.

In addition, the system 10 may include an imaging device (not shown) for monitoring the use of the system during treatment of a patient. For example, the system 10 may be placed within a magnetic resonance imaging (MRI) system, such as that disclosed in U.S. Pat. Nos. 5,247,935, 5,291,890, 5,368,031, 5,368,032, 5,443,068 issued to Cline et al., and U.S. Pat. Nos. 5,307,812, 5,323,779, 5,327,884 issued to Hardy et al., the disclosures of which are expressly incorporated herein by reference. Alternatively, an acoustic imaging device may be provided, or the transducer array 14 itself may be used for imaging, as is known to those skilled in the art.

Returning to FIG. 2, during use, a patient 90 may be disposed on the table 42 with water, ultrasonic conducting gel, and the like (not shown) applied between the patient 90 and the bag 46 or membrane 44, thereby acoustically coupling the patient 90 with the transducer array 14. The transducer array 14 may be oriented generally towards a target tissue region 92, e.g. within a tissue structure, such as a cancerous or benign tumor within an organ, e.g., a liver, kidney, pancreas, uterus, brain, and the like.

The acoustic path from the transducer array 14 to the target tissue region 92 may be analyzed, e.g., using MRI or ultrasound imaging, as explained above. For example, the acoustic path from each of the transducer elements 22 to the target tissue region 92 may be analyzed to determine tissue types or other characteristics that may affect the speed of the acoustic energy passing through intervening tissue between the transducer elements 22 and the target tissue region 92. Phase shift values may be determined for each of the transducer elements 22 to compensate for these variations in speed in order to maintain the focus of the acoustic energy substantially at the desired focal zone 17.

Optionally, if the analysis discovers that there are obstructions or high sensitivity volumes along an energy pass zone through which it is desired to prevent acoustic energy from passing (e.g., air-filled cavities, non-targeted thick bone, and the like), individual transducer elements 22 may be deactivated (e.g., have their amplitude set to zero (0)) in order to prevent acoustic energy from being transmitted by the relevant transducer elements 22.

Once any acoustic path analysis is complete, the controller 18 may be instructed to generate a treatment procedure, which may involve a single or multiple "sonications" (i.e., finite time periods during which the transducer array 14 is activated to deliver acoustic energy to a focal zone at a particular location within the target tissue region 92). The controller 18 and/or the operator may set the number and duration of sonications to be used to treat the target tissue region 92. The controller 18 may generate the tables described above and/or otherwise instruct the switch 20 in order to connect the output channels 34 of the driver 16 to respective transducer elements 22.

First, the controller 18 may assign phase shift values to the sets of drive signals that will be provided at each of the output channels 34 of the driver 16. Alternatively, the phase shift values of the sets of drive signals may be fixed, e.g., based upon phase errors required to achieve a predefined focus quality. For example, continuous wave (CW) acoustic beam forming in phased arrays requires the ability to control phase errors between different transducer elements to a particular level, e.g., better than $\lambda/10$, where $\lambda$ is the wavelength of the acoustic energy defining the acoustic beam. Because phase corrections are modulo $2\pi$, it would be desired to have phase accuracy better than $2\pi/10$. Given this desired accuracy, it may be able to attain the desired phase error corrections with as few as ten (10) phase values. It will be appreciated that more or fewer phase shift values, and consequently, output channels, may be provided. In an exemplary embodiment of a transducer array including two thousand (2,000) transducer elements, thirty two (32) phase values and output channels may be used.

The controller 18 may then determine desired phase shift values for the transducer elements 22 of the transducer array 14, taking into account focal zone shape, focal depth, steering angle, equal power distribution between drive channels, and tissue aberrations, as discussed above. One or more tables may be generated assigning each of the transducer elements 22 to one of the output channels 34, and the switch 20 may be set to connect the transducer elements 22 to the driver 16 based upon the generated tables.

Once the switch 20 is properly configured, the driver 16 may be activated in order to provide respective sets of drive signals to the transducer array 14. As explained above, the transducer elements 22 transform the drive signals into acoustic energy, represented by energy beam 15. As the acoustic energy 15 passes through the patient's body, the acoustic energy 15 is converted to heat at the focal zone 17, thereby raising the temperature of tissue within focal zone 17. The acoustic energy may be focused for sufficient time to raise the temperature of tissue within the focal zone 17 to necrose the tissue, while minimizing damage to surrounding tissue.

For example, the transducer array 14 may be activated for about ten seconds or more, e.g., between about two and forty (2-40) seconds, and preferably between about four and twenty seconds. Once a sonication is completed, the transducer array 14 may be deactivated, for example, for sufficient time to allow heat absorbed by the patient's tissue to dissipate, e.g., for about sixty (60) seconds. The transducer array 14 may then be focused at another focal zone within the target tissue region 92, for example, adjacent to the previous focal zone 17, and the process repeated until the entire target tissue region 92 is ablated.

Thus, during each sonication, the output channels 34 of the driver 16 may be connected to multiple transducer elements 22. This may substantially reduce the number of output channels 34 required for the transducer array 14, thereby substantially simplifying connection between the driver 16 and the transducer array 14. Preferably, the system 10 allows substantially more and smaller transducer elements to be provided for a given transducer array size and configuration, thereby enhancing the ability to steer the acoustic energy and focus the acoustic energy more precisely than conventional systems. Thus, it may be possible to steer the transducer array 14 to control the focal zone entirely using electronic steering, thereby eliminating the need for mechanical positioning systems and/or allowing simpler transducer configurations (e.g., planar arrays) to be used.

Although the systems and methods described herein have described ablating or otherwise treating tissue, the systems and methods of the present invention may also be used to perform other therapeutic or diagnostic procedures, e.g., ultrasound imaging and the like.

While the invention is susceptible to various modifications, and alternative forms, specific examples thereof have been shown in the drawings and are herein described in detail. It should be understood, however, that the invention is not to be limited to the particular forms or methods disclosed, but to the contrary, the invention is to cover all modifications, equivalents and alternatives falling within the scope of the appended claims.

What is claimed:

1. A system for focusing acoustic energy towards a target region, comprising:
    a transducer array comprising a plurality of "n" transducer elements;
    a controller for providing drive signals to the transducer array, the controller comprising a plurality of "m" output channels providing sets of drive signals having respective phase shift values, "m" being less than "n," wherein the controller is configured for assigning phase shift values to each of the transducer elements at least partially based upon an analysis of an acoustic path extending from each of the transducer elements to a desired focal zone within the target region; and a switch coupled to the output channels of the controller and to the transducer elements of the transducer array, the switch configured for connecting output channels to respective transducer elements in order to provide respective sets of drive signals to the respective transducer elements, whereby acoustic energy transmitted by the transducer array may be focused in a desired manner.

2. The system of claim 1, wherein the switch comprises a cross-point matrix or a multistage interconnection network (MIN).

3. The system of claim 1, wherein the switch comprises a plurality of "m" inputs coupled to the output channels of the controller, a plurality of "n" outputs coupled to the transducer elements, and a plurality of switching elements for connecting each of the inputs to one or more of the outputs.

4. The system of claim 1, wherein the switch is configured for coupling each output channel to more than one of the transducer elements.

5. The system of claim 1, further comprising an imaging apparatus for performing the acoustic path analysis, the controller coupled to the imaging apparatus for obtaining data related to the acoustic path analysis from the imaging apparatus.

6. The system of claim 1, wherein the controller is coupled to the switch for configuring the switch in order to connect the output channels to the respective transducer elements.

7. The system of claim 1, wherein the controller is configured for assigning each of the transducer elements to a respective output channel based upon one or more parameters related to a course of treatment of a target tissue region using the transducer array.

8. The system of claim 1, wherein the controller is configured for focusing the acoustic energy from the transducer array during a series of sonications into a target region, the switch being configurable before each sonication for focusing the acoustic energy into the target region to treat tissue within the target region.

9. The system of claim 1, wherein controller is configured for assigning the transducer elements to respective output channels via the switch in order to steer a focal zone within the target region in a desired manner.

10. A system for focusing acoustic energy towards a target region, comprising:
    a transducer array comprising a plurality of "n" transducer elements;
    a controller for providing drive signals to the transducer array, the controller comprising a plurality of "m" output channels providing sets of drive signals having respective phase shift values, "m" being less than "n," wherein the controller is configured for assigning the transducer elements to respective output channels based upon at least one of tissue aberrations caused by tissue between the transducer array and the focal zone, geometric tolerances of the transducer array, or impedance variations between the transducer elements; and
    a switch coupled to the output channels of the controller and to the transducer elements of the transducer array, the switch configured for connecting output channels to respective transducer elements in order to provide respective sets of drive signals to the respective transducer elements, whereby acoustic energy transmitted by the transducer array may be focused in a desired manner.

11. A method for delivering acoustic energy from a transducer array comprising a plurality of "n" transducer elements, the method comprising:
    assigning one of "m" phase shift values to each of the transducer elements, "m" being less than "n;" and delivering "m" sets of drive signals to the transducer array, each set of drive signals comprising a respective phase shift value selected from the "m" phase shift values, wherein the phase shift values are assigned to the transducer elements at least partially based on an analysis of an acoustic path from each of the transducer elements to the target region; and
    connecting the sets of drive signals to respective transducer elements based upon the phase shift values assigned to the respective transducer elements, whereby acoustic energy transmitted by the transducer elements may be focused in a desired manner towards a target region.

12. The method of claim 11, wherein connections between the sets of drive signals and respective transducer elements are reconfigured dynamically while acoustic energy is transmitted by the transducer elements.

13. The method of claim 11, wherein the phase shift value assigned to each of the transducer elements is compared to phase shift values of the sets of drive signals, and wherein each transducer element is assigned to a set of drive signals that has a phase shift value that approximates the phase shift value assigned to the respective transducer element.

14. The method of claim 11, wherein a table is generated during the acoustic path analysis that identifies the sets of drive signals assigned to each of the transducer elements, and wherein the table is used at least partially to configure a switch coupled to the transducer elements to connect the transducer elements to respective sets of drive signals.

15. A method for delivering acoustic energy from a transducer array comprising a plurality of "n" transducer elements, the method comprising:
    assigning one of "m" phase shift values to each of the transducer elements, "m" being less than "n;", wherein the phase shift values are assigned to the transducer elements at least partially based on analyzing an acoustic path from each of the transducer elements to the target region,
    delivering "m" sets of drive signals to the transducer array, each set of drive signals comprising a respective phase shift value selected from the "m" phase shift values; and
    connecting the sets of drive signals to respective transducer elements based upon the phase shift values assigned to the respective transducer elements, whereby acoustic energy transmitted by the transducer elements may be focused in a desired manner towards a target region, wherein the transducer array is disposed adjacent to a body, and wherein the transducer elements transmit acoustic energy into the body towards a focal zone within the target region when connected to the sets of drive signals.

16. The method of claim 15, wherein the acoustic energy is transmitted for sufficient time to ablate tissue within the target region.

17. The method of claim 15, wherein the phase shift values are assigned to the transducer elements at least partially to steer the focal zone within the target region relative to a central axis of the transducer array.

18. The method of claim 15, wherein the phase shift values are assigned to the transducer elements in order to focus the acoustic energy at multiple focal zones within the target tissue region.

19. A method for delivering acoustic energy from a transducer array comprising a plurality of "n" transducer elements to a target region, the method comprising:

providing "m" sets of drive signals, each set of drive signals comprising a respective phase shift value selected from "m" phase shift values, "m" being less than "n;"

analyzing an acoustic path from each of the transducer elements to the target region;

determining a phase shift value for each of the transducer elements based upon the acoustic path analysis;

connecting a first set of the drive signals to a first plurality of the transducer elements; and connecting a second set of the drive signals to a second plurality of the transducer elements, wherein each of the "m" sets of drive signals is connected to a plurality of the "n" transducer elements, each of the transducer elements is connected to one of the sets of drive signals, and connecting each of the transducer elements to one of the sets of drive signals is at least partially based upon the phase shift values of the respective transducer elements and the sets of drive signals, whereby acoustic energy is transmitted by the first and second plurality of transducer elements and focused in a desired manner into the target region.

20. The method of claim 19, wherein desired phase shift values are assigned to each of the transducer elements based upon at least one of a size, shape, and location of a focal zone within the target region, and wherein the desired phase shift values are combined with the phase shift values determined based upon the acoustic path analysis.

21. The method of claim 20, wherein the combined phase shift values for the transducer elements are compared to the phase shift values of the sets of drive signals, and wherein the transducer elements are assigned to respective sets of drive signals having phase shift values that approximate the combined phase shift values of the respective transducer elements.

22. The method of claim 19, wherein the acoustic energy transmitted by the first plurality of transducer elements is focused at a different location within the target region than the acoustic energy transmitted by the second plurality of transducer elements.

23. A method for delivering acoustic energy from a transducer array comprising a plurality of "n" transducer elements to a target region, the method comprising:

providing "m" sets of drive signals, each set of drive signals comprising a respective phase shift value selected from "m" phase shift values, "m" being less than "n;"

connecting a first set of the drive signals to a first plurality of the transducer elements; and connecting a second set of the drive signals to a second plurality of the transducer elements, whereby acoustic energy is transmitted by the first and second plurality of transducer elements and focused in a desired manner into the target region, wherein the first and second plurality of transducer elements are connected to first and second sets of drive signals based upon at least one of an analysis of an acoustic path extending from each of the transducer elements to a desired focal zone within the target region, tissue aberrations caused by tissue between the transducer array and the focal zone, geometric tolerances of the transducer array, or impedance variations between the transducer elements.

24. The method of claim 23, wherein the acoustic energy transmitted by the first plurality of transducer elements is focused at a different location within the target region than the acoustic energy transmitted by the second plurality of transducer elements.

* * * * *